(12) United States Patent
Dhanoa et al.

(10) Patent No.: US 6,409,988 B1
(45) Date of Patent: Jun. 25, 2002

(54) RADIOLABELED 1-ARYL PYRAZOLES, THE SYNTHESIS THEREOF AND THE USE THEREOF AS PEST GABA RECEPTOR LIGANDS

(75) Inventors: Daljit S. Dhanoa, West Chester; Sanath Meegalla, Devon, both of PA (US); Dario Doller, Branford, CT (US); Richard M. Soll, Lawrenceville, NJ (US)

(73) Assignee: 3-Dimensional Pharmaceuticals, Inc., Exton, PA (US)

( * ) Notice: Subject to any disclaimer, the term of this patent is extended or adjusted under 35 U.S.C. 154(b) by 15 days.

(21) Appl. No.: 09/606,051

(22) Filed: Jun. 29, 2000

Related U.S. Application Data
(60) Provisional application No. 60/141,844, filed on Jul. 1, 1999.

(51) Int. Cl.[7] .................. A61K 51/00; C07D 231/10

(52) U.S. Cl. .................. 424/1.81; 548/377.1

(58) Field of Search .............. 424/1.81, 1.65; 548/377.1, 379.7

(56) References Cited

U.S. PATENT DOCUMENTS

| | | |
|---|---|---|
| 1,685,407 A | 9/1928 | Mannich |
| 3,235,360 A | 2/1966 | Soboczenski .................. 71/2.5 |
| 3,326,662 A | 6/1967 | Toyosato et al. ............. 71/2.5 |
| 3,364,227 A | 1/1968 | Robinson .................... 260/310 |
| 3,637,738 A | 1/1972 | Gschwend et al. ......... 260/311 |
| 3,818,026 A | 6/1974 | Boesch ................... 260/307 A |
| 3,836,539 A | 9/1974 | Boesch ................... 260/307 A |
| 3,846,440 A | 11/1974 | Boesch et al. .......... 260/307 A |
| 3,883,550 A | 5/1975 | Goddard ................. 260/310 C |
| 4,059,434 A | 11/1977 | Wolf ............................ 71/92 |

(List continued on next page.)

FOREIGN PATENT DOCUMENTS

| | | |
|---|---|---|
| DE | 19511269 A1 | 10/1995 |
| DE | 19518054 A1 | 9/1996 |
| DE | 19544799 A1 | 6/1997 |
| DE | 197 56 115 A1 | 6/1999 |
| EP | 0 138 527 A2 | 4/1985 |
| EP | 0 234 119 A1 | 9/1987 |
| EP | 0 350 311 A1 | 1/1990 |
| EP | 0 392 499 A2 | 10/1990 |
| EP | 0 398 499 A2 | 11/1990 |
| EP | 0 412 849 A2 | 2/1991 |
| EP | 0 418 016 A1 | 3/1991 |
| EP | 0 558 999 A2 | 9/1993 |
| EP | 0 659 745 A1 | 6/1995 |

(List continued on next page.)

OTHER PUBLICATIONS

Cole, L.M. et al., "Action of Phenylpyrazole Insecticides at the GABA–Gated Chloride Channel," *Pesticide Biochem. Biophys.* 46:47–54 Academic Press, New York, NY (1993).

Finkelstein, B.L. and C.J. Strock, "Synthesis and Insecticidal Activity of Novel Pyrazole Methanesulfonates," *Pestic. Sci.* 50:324–328 John Wiley & Sons, New York, NY (1997).

Ando, I. et al., "Synthesis and Biological Activity of Cyclic Imide Derivatives and Related Compounds," *Agric. Biol. Chem.* 53:2001–2003, Japan Society for Bioscience, Biotechnology and Agrochemistry, Japan (1989).

Baraldi, P.G. et al., "A Mild One–Pot Synthesis of Thieno [3,4–c]pyrazoles and Their Conversion into Pyrazole Analogs of o–Quinodimethane," *Synthesis* (9):1331–1334, Thieme, New York, NY (Sep. 1998).

Bardou, L. et al., "XVI.—Pyrazoles bicycliques," *Bulletin de la Société Chimique de France* (1):289–294, Société Chimique de France, Paris, France (1967).

(List continued on next page.)

*Primary Examiner*—Michael G. Hartley
(74) *Attorney, Agent, or Firm*—Sterne, Kessler, Goldstein & Fox P.L.L.C.

(57) ABSTRACT

The present invention is directed to radiolabeled compounds of Formula I:

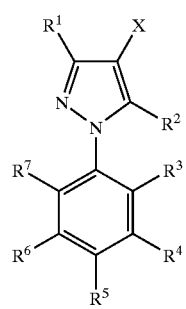

or salts thereof, where $R^1$ represents $R^8$, $R^8O$, $R^8SO_2$, $R^8SO$ or $R^8S$ in which $R^8$ is tritiated or deuterated methyl;

X is halo, cyano, $C_{1-6}$ alkoxycarbonyl, $C_{2-6}$ alkynyl, optionally substituted $C_{6-14}$ aryl or an optionally substituted 5- to 7-membered heteroaromatic ring linked to thiazole via a carbon-carbon bond;

$R^2$ is hydrogen or amino; and $R^3$–$R^7$ are defined in the specification.

The invention is also directed to methods of using such compounds for demonstrating specific insect GABA receptors, qualitatively screening for compounds acting on an insect GABA receptor or quantitatively assaying concentrations of a compound acting on an insect GABA receptor.

16 Claims, No Drawings

U.S. PATENT DOCUMENTS

| | | | |
|---|---|---|---|
| 4,108,628 A | 8/1978 | Wolf | 71/92 |
| 4,111,681 A | 9/1978 | Goddard | 71/92 |
| 4,124,373 A | 11/1978 | Wolf | 71/92 |
| 4,331,678 A | 5/1982 | De'Ath et al. | 424/273 |
| 4,666,507 A | 5/1987 | Yanagi et al. | 71/92 |
| 4,695,312 A | 9/1987 | Hayase et al. | 71/92 |
| 4,740,231 A | 4/1988 | Gehring et al. | 71/92 |
| 5,104,994 A | 4/1992 | Roberts et al. | 548/376 |
| 5,134,155 A | 7/1992 | Connolly et al. | 514/403 |
| 5,232,940 A | 8/1993 | Hatton et al. | 514/407 |
| 5,306,694 A | 4/1994 | Phillips et al. | 504/253 |
| 5,387,693 A | 2/1995 | Connolly et al. | 548/360.1 |
| 5,487,976 A | 1/1996 | Soderlund et al. | 435/7.21 |
| 5,637,607 A | 6/1997 | Pilato et al. | 514/404 |
| 5,707,936 A | 1/1998 | Oberdorf et al. | 504/253 |
| 5,814,652 A | 9/1998 | Wu | 514/404 |
| 5,849,778 A | 12/1998 | Heil et al. | 514/403 |
| 5,869,517 A | 2/1999 | Müller et al. | 514/407 |
| 6,069,157 A | 5/2000 | Banks | 514/341 |

FOREIGN PATENT DOCUMENTS

| | | |
|---|---|---|
| EP | 0 152 286 A1 | 8/1995 |
| EP | 0 745 684 A1 | 12/1996 |
| EP | 0 846 686 A1 | 6/1998 |
| FR | 2301250 | 10/1976 |
| JP | 59181259 | 10/1984 |
| JP | 6041667 | 3/1985 |
| JP | 60-233061 | 11/1985 |
| JP | 61-165373 | 7/1986 |
| JP | 63-287766 | 11/1988 |
| JP | 8208620 | 8/1996 |
| KR | 917886 | 10/1991 |
| WO | WO 92/13451 | 8/1992 |
| WO | WO 93/06089 | 4/1993 |
| WO | WO 93/19054 | 9/1993 |
| WO | WO 93/21160 | 10/1993 |
| WO | WO 94/13643 | 6/1994 |
| WO | WO 94/13644 | 6/1994 |
| WO | WO 94/13661 | 6/1994 |
| WO | WO 94/13677 | 6/1994 |
| WO | WO 94/21606 | 9/1994 |
| WO | WO 95/22530 | 8/1995 |
| WO | WO 95/33727 | 12/1995 |
| WO | WO 98/22442 A2 | 5/1998 |

OTHER PUBLICATIONS

Bauer, V.J. et al., "Synthesis Alkylation, and Oxidation of Theino[3,4–c]–and –[3,2–c]pyrazoles," *J. Med. Chem.* 14:454–456, American Chemical Society, Washington, DC (1971).

Chou, T.–s. and Chang, R.–C., "A Novel Route to the Preparation of Pyrazole Analogues of o–Xylylene," *J. Org. Chem.* 58:493–496, American Chemical Society, Washington, DC (1993).

Chou, T.–s. and Chang, R.–C., "Synthesis and Reactions of N–Substituted Pyrazolo–3–Sulfolenes," *Heterocycles* 36:2839–2850, Elsevier Science, New York, NY (1993).

Connolly, P.J. et al., "HMG–CoA Reductase Inhibitors: Design, Synthesis, and Biological Activity of Tetrahydroindazole–Substituted 3,5–Dihydroxy–6–heptenoic Acid Sodium Salts," *J. Med. Chem.* 36:3674–3685, American Chemical Society, Washington, DC (1993).

Duncan, D.C. et al., "The Preparation of N–Carboalkoxypyrazoles and N–Phenylpyrazoles from C($\alpha$)–Dianions of Carboalkoxyhydrazones and Phenylhydrazones," *J. Heterocyclic Chem.* 24:555–559, Hetero Corporation, Provo, Utah (1987).

Elguero, J. et al., "XIV.—Étude UV de pyrazoles," *Bulletin de la Société Chimique de France* (12):3744–3752, Société Chimique de France, Paris, France (1966).

Jacquier, R. and Maury, G., "(Dinitro–2', 4' phényl)–1 pyrazoles dérivant de l'hydroxyméthylène–2 cycloheptanone et de l'hydroxyméthylène–3 camphre (Note de Laboratoire)," *Bulletin de la Société Chimique de France* (1):295–297, Société Chimique de France, Paris, France (1967).

Jacquier, R. and Maury, G., "XVII.—Synthèses et étude des (dinitro–2',4' phényl)–1 pyrazoles isomères dérivant d'acétyl–2 cyclanones (Première partie)," *Bulletin de la Société Chimique de France (1):306–315, Société Chimique de France*, Paris, France (1967).

Jacquier, R. and Maury, G., "XIX.—Synthéses et étude des (dinitro–2',4' phényl)–1 pyrazoles isoméres dérivant d'acétyl–2 cyclanones (Deuxième partie)," *Bulletin de la Société Chimique de France* (1):316–320, Société Chimique de France, Paris, France (1967).

Lyga, J.W. et al., "Synthesis, Mechanism of Action, and QSAR of Herbicidal 3–Substituted–2–aryl–4,5,6,7–tetrahyroindazoles," *Pestic. Sci* 42:29–36, John Wiley & Sons, Inc., New York, NY (1994).

Malik, O.P. et al., "Synthesis of 2,3–Substituted 4,5,6,7–Tetrahydro–2H–Indazoles; 2,4,5,6,7,8–Hexahydrocyclohepta(C) Pyrazoles and Their $\omega$–t–Aminoalkyl Enol Ethers," *Harayana agric. Univ. J. Res.* 10:218–221 (1980).

Schenone, S. et al., "2–Aryl–3–Phenylamino–4,5–Dihydro–2H–Benz[g]indazoles with Antiarrhythmic and Local Anaesthetic Activities," *Il Farmaco* 50:179–182, Società Chimica Italiana, Rome, Italy (1995).

Strakova, I.A. et al., "Synthesis and Reactions of 1–(2–Pyridyl)–3–Methyl–4–Chloro–5–Formyl–6,7–Dihydroindazoles," *Chem. Heterocyclic Compounds* 34:669–673, Plenum Publishing Corporation, London, England (1998).

Wang, Q. et al., "On the Reaction of 1–Aza–2–azoniaallene Salts with Acetylenes," *Chem. Ber.* 127:541–547, VCH Verlagsgesellschaft mbH, Weinheim, Germany (1994).

Williams, R.P. et al., "Synthesis and Alkylation of Tetrahydrocyclopentapyrazolols," *J. Med. Chem.* 13:773–775, American Chemical Society, Washington, DC (1970).

Yoichi, I., "Phenylpyrazole Derivatives and Noxious Life Controlling Agent," *Patent Abstracts of Japan*, Publication No. 05262741, European Patent Office (1993).

Yukiaki, M., "Aminopyrazole Derivative, Its Production and Use," *Patent Abstracts of Japan*, Publication No. 08208620, European Patent Office (1996).

Yukiaki, M., "Pyrazole Derivative, Its Use," *Patent Abstracts of Japan*, Publication No. 08311036, European Patent Office (1996).

CAPLUS Accession No. 1967:473550, Document No. 67:73550, CAPLUS English language abstract, American Chemical Society, Washington, DC, for Document AS5, Bardou, L. et al., *Bulletin de la Société Chimique de France* (1):289–294, Société Chimique de France, Paris, France (1967).

CAPLUS Accession No. 1967:80664, Document No. 66:80664, CAPLUS English language abstract, American Chemical Society, Washington, DC, for Document AS7, Elguero, J. et al., *Bulletin de la Société Chimique de France* (12):3744–3752, Société Chimique de France, Paris, France (1966).

CAPLUS Accession No. 1967:403028, Document No. 67:3028, CAPLUS English language abstract, American Chemical Society, Washington, DC, for Document AT7, Jacquier, R. and Maury, G., *Bulletin de la Société Chimique de France* (1):295–297, Société Chimique de France, Paris, France (1967).

CAPLUS Accession No. 1967:508588, Document No. 67:108588, CAPLUS English language abstract, American Chemical Society, Washington, DC, for Document AR8, Jacquier, R. and Maury, G., *Bulletin de la Société Chimique de France* (1):306–315, Société Chimique de France, Paris, France (1967).

CAPLUS Accession No. 1967:473551, Document No. 67:73551, CAPLUS English language abstract, American Chemical Society, Washington, DC, for Document AS8, Jacquier, R. and Maury, G., *Bulletin de la Société Chimique de France* (1):316–320, Société Chimique de France, Paris, France (1967).

RADIOLABELED 1-ARYL PYRAZOLES, THE SYNTHESIS THEREOF AND THE USE THEREOF AS PEST GABA RECEPTOR LIGANDS

This application claims benefit under 35 U.S.C. §119(e) of U.S. Provisional Application No. 60/141,844, filed Jul. 1, 1999.

BACKGROUND OF THE INVENTION

1. Field of the Invention

The present invention relates to novel radiolabled compounds, and to a process for their manufacture. The invention is further directed to compositions comprising these labeled compounds, as well as to methods of using these compounds.

2. Related Art

γ-Aminobutyric acid (GABA) receptors are intrinsic membrane glycoproteins in vertebrate and invertebrate neuronal tissues that are members of the ligand-gated ion channel superfamily of receptors. GABA receptors play a major role in the inhibition of central nervous system (CNS) neuronal activity due to the widespread distribution of GABA-releasing and GABA-receptive neurons.

Vertebrate GABA receptors can be divided into two major classes: the $GABA_A$ and $GABA_C$ receptor subtypes, and $GABA_B$ receptor types, which are distinguished by differences in their effector mechanisms and pharmacology (Knapp, R. J., et al., *Neurochem. Res.* 15:105–112 (1990)). $GABA_A$ and $GABA_C$ receptors are transmitter-operated chloride channels that are activated by GABA to open their chloride channel while $GABA_B$ receptors are thought to mediate changes in cyclic AMP levels through the activation of phospholipase activity (Eldefrawi, A. T. and Eldefrawi, M. E., *FASEB J.* 1:262–271 (1987); Knapp, R. J., et al., *Neurochem. Res.* 15:105–112 (1990)). The $GABA_A$ receptor and its associated chloride ion channel make up the so-called $GABA_A$ receptor-channel complex.

GABA receptors play an important role in the chemical control of insects, such as fleas, ticks, house flies, fruit flies, plant bugs, boll weevils, grasshoppers, cockroaches, mosquitoes, beetles, locust and moths (Hainzl, D., et al., *Chem. Res. Toxicol.* 11: 1529–1535 (1998)). To date, all insect GABA receptors studied gate a fast acting chloride ion conductance. Although they appear to share many of the properties of $GABA_A$-type receptors in the vertebrate CNS, the majority of receptors in the insect nervous system appear to be bicuculline-, pitrazepin- and RU5135-insensitive (Anthony, N. M., et al., *Comp. Mol. Neurobiol.*, Pichon, Y., ed., Birkhäuser Verlag, Basel, Switzerland, pp. 172–209 (1993); Wafford, K. A., et al., *J. Neurochem.* 48:177–180 (1987)). These findings indicate that insect GABA receptors contain several drug binding sites with structural and target site specificities that are different from vertebrate receptor-binding sites (Hainzl, D., et al., *Chem. Res. Toxicol.* 11:1529–1535 (1998)). Selective insecticides, e.g., insecticides with favorable selective toxicity for insects relative to vertebrates, are based in part on this target-site specificity between the GABA receptors of insects and $GABA_A$ receptors of vertebrates (Moffat, A. S., *Science* 261:550–551 (1993); Hainzl, D., et al., *Chem. Res. Toxicol.* 11:1529–1535 (1998)).

Radiolabeled ligand binding studies have expanded our knowledge of insect GABA receptor pharmacology. Within the GABA receptor three distinct binding sites have been identified: the GABA receptor agonist binding site, a benzodiazepine binding site and a convulsant binding site (Lummis, S. C. R., *Comp. Biochem. Physiol.* 95C:1–8 (1990); Rauh, J. J., et al., *TiPS* 11:325–329 (1990)). The convulsant binding site of GABA receptors in insects is the major target site for many of the drugs and insecticides currently on the market.

Convulsant drugs and insecticides act at the GABA receptor in insect brain, ganglia and muscle as noncompetitive blockers. Inhibition of GABA receptors in insects produces neurotoxicity (e.g., convulsions, paralysis, coma and death). In the early 1980s, the insecticides lindane and cyclodienes (e.g., dieldrin) were shown to antagonize the action of GABA in stimulating chloride uptake by various insect nerve and muscle preparations (Narahashi, T., *Pharmacol. Toxicol.* 78:1–14 (1996)). GABA receptors in insects are also blocked by picrotoxin, phenylpyrazole insecticides (e.g., Fipronil®), bicyclophosphorous esters (e.g., t-butylbicyclophosphoronthionate), and bicycloorthobenzoates (4-n-propyl-4'-ethynylbicycloorthobenzoate) (U.S. Pat. No. 5,853,002). These insecticides block transmission of signals by GABA, and are very effective on a wide range of economically important pests.

Unfortunately, many potent insecticides and their derivatives also act at the $GABA_A$ receptors of host animals. For example, fipronil sulfone and desulfinyl fipronil, a metabolite and photoproduct of fipronil, respectively, are not only toxic to insects, but also to upland game birds, freshwater fish and invertebrates, and waterfowl. In addition, fipronil itself is a toxicant for mammals even without oxidation to the sulfone (Hainzl, D., et al., *Chem. Res. Toxicol.* 11:1529–1535 (1998)).

Target-site specificity between the GABA receptors of insects and mammals can be assayed with the radioligand 4'-ethynyl-4-n-[2,3-$^3H_2$]-propylbicycloorthobenzoate ([$^3H$] EBOB, 2). Compounds 3–5, were also developed as radioligands for the GABA-gated chloride channel. Casida,, J. E., *Arch. Insect Biochem. & Physiol.* 22:13 (1993); and Palmer, C. J. & Casida, J. E., *J. Labelled Compounds & Radiopharmaceuticals* 29:829 (1991).

The development of suitable radioligands constitutes a major step in deepening the understanding of the GABA-gated chloride channel.

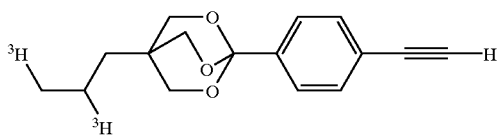

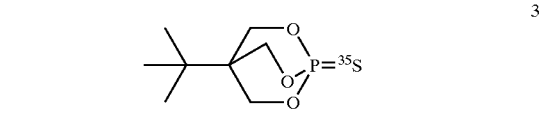

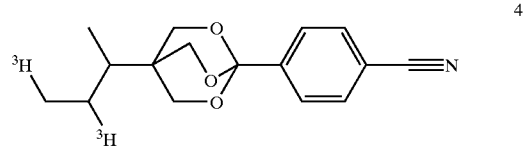

-continued

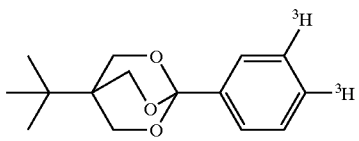

Radioligands 3–5, among others, have proven unsatisfactory for the insect receptor. This was attributed to their low insecticidal activity. Radioligand 2 is presently used. However, it is unstable and must be periodically purified.

Insect neuronal GABA receptors exhibit pharmacological similarity to mammalian $GABA_A$ receptors, but also exhibit critical differences, for example in the potency order for agonists and antagonists. Adverse toxicology has led to significant restrictions on the use of many insecticides. Further, the selection of resistant pest strains has resulted in the ineffectiveness of some chloride channel blockers and activators as insecticides. A better understanding of the insect GABA receptor is necessary to develop insecticides that are not subject to resistance, and that exhibit better selectivity and enhanced environmental safety.

A need exists in the art for a radiolabeled compound that binds to the pest GABA gated chloride ion channel, and possesses chemical stability.

SUMMARY OF THE INVENTION

A first aspect of the present invention is directed to radiolabeled compounds of Formula I.

A second aspect of the invention is directed to a method of demonstrating specific pest GABA receptors, qualitatively screening for compounds acting on a pest GABA receptor or quantitatively assaying concentrations of a compound acting on a pest GABA receptor, comprising contacting a pest GABA receptor with a compound of Formula I, or a salt thereof.

A third aspect of the invention is directed to a composition comprising at least one compound of Formula I, or a salt thereof, and an acceptable carrier or diluent.

A fourth aspect of the present invention is directed to methods for synthesizing radiolabeled compounds of Formula I.

DETAILED DESCRIPTION OF THE PREFERRED EMBODIMENTS

A first aspect of the present invention is radiolabeled compounds of Formula I:

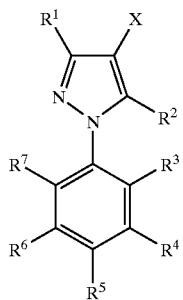

I or a salt thereof, where $R^1$ represents $R^8$, $R^8O$, $R^8SO_2$, $R^8SO$ or $R^8S$ in which $R^8$ is tritiated methyl, deuterated methyl, [$^{13}C$]methyl or [$^{14}C$]methyl;

X is halo, cyano, $C_{1-6}$ alkoxycarbonyl, $C_{2-6}$ alkynyl, optionally substituted $C_{6-14}$ aryl or an optionally substituted 5- to 7-membered heteroaryl group linked to thiazole via a carbon-carbon bond;

$R^2$ is hydrogen or amino; and $R^3$–$R^7$ each represent hydrogen, halogen, straight- or branched-chain $C_{1-4}$ alkyl or $C_{1-4}$ alkoxy, either of which is unsubstituted or substituted by one or more halogen atoms, straight- or branched-chain $C_{1-4}$ alkylthio or $C_{1-4}$ alkylsulphinyl, either of which is substituted by one or more halogen atoms, nitro, cyano, or straight- or branched-chain $C_{1-4}$ alkylsulphonyl group which is unsubstituted or substituted by one or more halogen atoms.

Preferred $R^1$ groups include $R^1$ is —$SC^3H_3$, —$SOC^3H_3$, —$SO_2C^3H_3$, —$S^{14}CH_3$, —$S^{13}CH_3$, —$S^{13}C^2H_3$, and —$SC^2H_3$.

Preferred X include cyano, chloro, iodo, $C_{1-4}$ alkoxycarbonyl (such as ethoxycarbonyl and methoxycarbonyl), $C_{2-4}$ alkynyl (such as ethynyl and propynyl). Additional preferred X include the following optionally substituted aryl and heteroaryl groups: phenyl, naphthyl, pyridyl, thienyl, furanyl, isoxazolyl, thiazolyl, isothiazolyl, indolizinyl, isoindolyl, indolyl, indazolyl, quinolizinyl, quinolinyl, and isoquinolinyl. Preferred optional substituents on the Ar group include one or more of halogen, $C_{1-4}$ alkyl, $C_{1-4}$ alkoxy, $C_{1-4}$ haloalkoxy, $C_{1-4}$ alkoxycarbonyl, nitro, amino, cyano, $C_{1-4}$ alkylthio, $C_{1-4}$ alkylsulfinyl or $C_{1-4}$ alkylsulfonyl.

Suitable values of X, when X is an optionally substituted aryl or heteroaryl group include 3-methyloxadiazin-5-yl, thiophen-2-yl; thiophen-3-yl, 5-methylthiophen-2-yl, 4-methylthiophen-2-yl, 5-chlorothiophen-2-yl, 4-chlorothiophen-2-yl, 5-methylcarbonylthiophen-2-yl, benzothiophen-2-yl, pyrimidin-6-yl, pyrazin-6-yl, phenyl, 2-methylphenyl, 2-fluorophenyl, 2-chlorophenyl, 2-trifluoromethylphenyl, 2-cyanophenyl, 2-methoxyphenyl, 2-methylthiophenyl, 2,4-dimethoxyphenyl, 3-methylphenyl, 3-isopropylphenyl, 3-methoxyphenyl, 2-fluorophenyl, 2-chlorophenyl, 2-trifluoromethylphenyl, 2-cyanophenyl, 2-methoxyphenyl, 2-methylthiophenyl, 3,5-di(trifluoromethyl)phenyl, 3-chloro-4-fluorophenyl, 3,4-dimethoxyphenyl, 3,4,5-trimethoxyphenyl, 1,3-benzodioxazol-5-yl, 4-methylphenyl, 4-fluorophenyl, 4-chlorophenyl, 4-bromophenyl, 4-trifluoromethylphenyl, 4-cyanophenyl, biphenyl, 4-isopropylphenyl, 4-methoxyphenyl, and 4-methylthiophenyl.

X is most preferably CN.

$R^2$ is hydrogen or $NH_2$.

Preferred $R^3$ values are halogen, especially chloro. A preferred $R^4$ value is hydrogen. Preferred $R^5$ values are hydrogen, $C_{1-6}$ alkyl optionally substituted by one or more halogen atoms, $C_{1-6}$ alkoxy, optionally substituted by one or more halogen atoms or $SF_5$. A preferred $R_6$ value is hydrogen and preferred $R^7$ value is halogen, especially chloro. More preferred combinations result in the following substitution patterns on the 1-phenyl ring: 2,4,6-trichloro-, 2-6-dichloro-4-difluoromethoxy-, 2-chloro-4-trifluoromethyl-, 2-bromo-6-4-trifluoromethyl-, 2,6-dibromo-4-trifluoromethyl- or 2-bromo-4-trifluoromethyl-, with 2,6-dichloro-4-trifluoromethyl and 2,6-dichloro-4-trifluoromethoxy being most preferred.

An example of a suitable compound is:

compound 1,4-cyano-1-(2,6-dichloro-4-trifluorophenyl)-3-[$^3H_3$]methylthiopyrazol-5-ylamine.

Compound 1 binds to the housefly GABA receptor with high affinity ($IC_{50}$=8 nM, for displacement of 2.6 nM of $^3$H-EBOB) and can be radiolabeled at high specific activity (>70 Ci/mmol). These are two highly desirable requirements for a new radioligand. In addition, the compound is chemically stable; therefore avoiding periodic purification steps.

The term "optionally substituted" when not otherwise explicitly provided for refers to the replacement of a hydrogen (or in the case of keto, two hydrogens) in a particular radical, with a functional group selected from the group consisting of halogen, trifluoromethyl, hydroxy, $C_{1-4}$ alkoxy, $C_{1-4}$ alkylthio, $C_{1-4}$ alkylsulfinyl, amino, nitro, cyano, $C_{2-6}$ carboxyalkyl, amidine, tetrazolyl, mono- or di-($C_{1-6}$) alkylamino, mono- or di-($C_{6-10}$)arylamino, $C_{6-10}$ arylthio, $C_{6-10}$ arylsulfonyl, $C_{6-10}$ arylsulfinyl, oxime, $C_{6-10}$ aryl hydrazone, aminocarbonyl, mono- or di-($C_{1-6}$) alkylaminocarbonyl, carboxyamino, $C_{1-6}$ alkoxycarbonylamino, $C_{6-10}$ aryloxycarbonylamino, $C_{7-11}$ aralkoxycarbonylamino, and mono- or di-($C_{1-6}$) alkylaminothiocarbonyl.

The term "alkyl" as employed herein by itself or as part of another group refers to both straight and branched chain radicals of up to 10 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, and decyl. Preferably, the alkyl chain is 2 to 8 carbon atoms in length, more preferably from 2 to 4 carbon atoms in length.

The term "alkynyl" is used herein to mean a straight or branched chain radical of 2–10 carbon atoms, unless the chain length is limited thereto, wherein there is at least one triple bond between two of the carbon atoms in the chain, including, but not limited to, acetylene, 1-propylene, 2-propylene, and the like. Preferably, the alkynyl chain is 2 to 8 carbon atoms in length, more preferably from 2 to 4 carbon atoms in length.

In all instances herein where there is an alkynyl moiety as a substituent group, the unsaturated linkage, i.e., the acetylene linkage is preferably not directly attached to a nitrogen, oxygen or sulfur moiety.

The terms "alkoxy" refers to any of the above alkyl groups linked to an oxygen atom.

The term "aryl" as employed herein by itself or as part of another group refers to monocyclic or bicyclic aromatic groups containing from 6 to 14 carbons in the ring portion, preferably 6–10 carbons in the ring portion, such as phenyl, naphthyl, tetrahydronaphthyl, or biphenyl.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroatoms (where examples of heteroaryl groups are: thienyl (thiophenyl), benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

The term "halogen" or "halo" as employed herein by itself or as part of another group refers to chlorine, bromine, fluorine or iodine with chlorine being preferred.

The term "heteroatom" is used herein to mean an oxygen atom ("O"), a sulfur atom ("S") or a nitrogen atom ("N"). It will be recognized that when the heteroatom is nitrogen, it may form an $NR^yR^z$ moiety, wherein $R^y$ and $R^z$ are, independently from one another, hydrogen or $C_1$ to $C_8$ alkyl, or together with the nitrogen to which they are bound, form a saturated or unsaturated 5-, 6-, or 7-membered ring.

By the term "salts" is meant salts the cations of which are known and accepted in the art for the formation of organic acids for receptor studies or for agricultural or horticultural use. When intended for application to vertebrates, the salts with bases used will be non-toxic. By the term "non-toxic" is meant salts with bases the cations of which are innocuous to the vertebrates at the doses administered.

Preferably, the salts are water-soluble. Suitable salts with bases include alkali metal (e.g., sodium and potassium), alkaline earth metal (e.g., calcium and magnesium), ammonium and amine (e.g., diethanolamine, triethanolamine, octylamine, morpholine and dioctylmethylamine) salts. Where reference is made in the present specification to the compounds of Formula I such reference is intended to include also the salts with acceptable bases of compounds of Formula I where appropriate.

The term "pest" or "pests" is used herein to mean undesired arthropods, for example, insects and arachnids, that are harmful to plants and animals (hosts) which are susceptible to infestation by a given undesired arthropod.

The phrase "effective amount" is used herein to mean an amount effective to achieve the intended purpose. While individual needs vary, determination of optimal ranges of active components is within the skill of the art.

Compositions and Methods of Use

A second aspect of the present invention is directed to methods of using the compounds of Formula I in qualitative and quantitative assays for pest GABA receptors. Preferably the compounds are employed in assays for GABA receptors of arthropod pests, such as insects and arachnids, preferably fleas and ticks. Such assays can be employed to measure the presence or amount of GABA receptors, or to quantitatively or qualitatively measure binding of radiolabeled compound in binding assays at the GABA-gated chloride channel. Thus, the methods of the invention can be used to demonstrate and characterize pest GABA receptors, preferably specific insect GABA receptors. Such assays will be valuable to the veterinary industry to screen for novel compounds acting on these receptors, and to assay concentrations and amounts of such compounds.

The labeled compounds are of value in insecticide and veterinary research and development and also as active ingredients of insecticidal compositions. The compounds can be used to evaluate the mechanism of insect neurotransmitter regulation and function, both in vitro and in vivo.

A third aspect of the invention is directed to compositions comprising at least one compound of Formula I, or a salt thereof, and one or more acceptable carriers or diluents.

Labeled compounds can be made into veterinary compositions by combination with appropriate carriers or diluents. For example, labeled compounds of the invention can be dissolved in oils, propyleneglycol or other solvents commonly used to prepared injectable solutions. Suitable carriers include physiological saline, polyethylene glycol, ethanol, sesame oil, cremophor and isopropyl myristate.

The following methods and excipients are merely exemplary and in no way limit the invention.

The labeled compounds of the present invention in veterinary dosage forms may be used in the form of their labeled non-toxic salts, and also may be used alone or in appropriate association, as well as in combination with other active veterinary compounds.

Compositions suitable for administration to vertebrates or man include preparations suitable for oral, parenteral, percutaneous, e.g. pour-on, spot-on or other topical administration.

Compositions for oral administration comprise one or more of the compounds of Formula I in association with non-toxic veterinary carriers or coatings and include, for example, chewable treats, tablets, pills, capsules, pastes, gels, drenches, medicated feeds, medicated drinking water, medicated dietary supplements, slow-release boluses or other slow-release devices intended to be retained within the gastro-intestinal tract. Any of these may incorporate active ingredient contained within microcapsules or coated with acid-labile or alkali-labile or other pharmaceutically acceptable enteric coatings. Feed premixes and concentrates containing compounds of the present invention for use in preparation of medicated diets, drinking water or other materials for consumption by animals may also be used.

Compositions for parenteral administration include solutions, emulsions or suspensions in any suitable veterinary vehicle and solid or semisolid subcutaneous implants or pellets designed to release active ingredient over a protracted period and may be prepared and made sterile in any appropriate manner known to the art.

Compositions for percutaneous and topical administration include sprays, dusts, baths, dips, showers, jets, greases, shampoos, creams, wax-smears, or spot-on or pour-on preparations and with the aid of shaped articles which contain active compound, such as neck bands, ear tags, tail tags, limb bands, halters, marking devices and the like devices (e.g. ear tags) attached externally to animals in such a way as to provide local or systemic arthropod control.

Solid or liquid baits suitable for controlling arthropods comprise one or more compounds of Formula I and a carrier or diluent which may include a food substance or some other substance to induce consumption by the arthropod.

Medicated feeds which comprise a compound of Formula I and arthropodicidally-acceptable salts thereof and an edible carrier or diluent form an additional feature of the present invention.

Liquid compositions include water miscible concentrates, emulsifiable concentrates, flowable suspensions, wettable or soluble powders containing one or more compounds of Formula I which may be used to treat substrates or sites infested or liable to infestation by arthropods including premises, outdoor or indoor storage or processing areas, containers or equipment and standing or running water.

Solid homogenous or heterogenous compositions containing one or more compounds of Formula I, for example granules, pellets, briquettes or capsules, may be used to treat standing or running water over a period of time. A similar effect may be achieved using trickle or intermittent feeds of water dispersible concentrates.

The labeled compounds of the present invention may be formulated into preparations for injections by dissolving, suspending, or emulsifying them in aqueous solvents such as normal saline, Dextrose 5%, or non-aqueous solvent, such as vegetable oil, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The labeled compounds of the invention may be combined with other compounds having the desired effect.

The desirable dose of the labeled compounds of the present invention varies with the subject, drug form, method and period of administration. However, in order to obtain desirable effects for in vivo administration, generally it is recommended to administer $1 \times 10^{-3}$ to 10 mg/kg, preferably $1 \times 10^{-3}$ to 0.1 mg/kg, body weight of the labeled compounds of the present invention for single application, or less upon multiple application. In terms of composition, labeled compounds should be present between 0.0001 to 10% by weight, preferably 0.0001 to 1% by weight.

For the measurement of binding in vitro the labeled compounds should be present in the binding mixture at a concentration of between $10^{-13}$ M to $10^{-6}$ M, preferably $10^{-11}$ M to $10^{-8}$ M. For storage and dilution, the compounds may be more concentrated, preferably at least 100-fold more concentrated, and concentrations of 1 M or greater are acceptable. Suitable solvents before addition to the assay mixture include dimethylsulfoxide, ethanol or methanol. For storage, these solvents or mixtures with less non-polar solvents such as ethyl acetate are suitable.

The present invention may be useful to demonstrate specific pest GABA receptors, preferably insect GABA receptors, more preferably fly, flea or tick GABA receptors, as well as to screen for novel products acting on these receptors, and to assay concentrations and amounts of such compounds.

Scatchard and Hill transformations are performed by the Equilibrium Binding Data Analysis program referred to as EBDA. Data are further analyzed by the curvilinear regression program LIGAND (Munson, R. J. and Rodbard, D., *Anal. Biochem.* 107:220–239 (1980)).

Accordingly, one use of the labeled compounds of the invention is the characterization of specific receptor binding.

Another use of the labeled compounds of the invention is as an alternative to animal testing for the evaluation of GABA structure-activity relations. The above receptor assay is performed at a fixed concentration of labeled compound of Formula I and at increasing concentrations of a test compound in a competition assay as described above. The assay would find application in the detailed evaluation of the many derivatives produced by the pharmaceutical industry in its attempts to develop unique compounds as pest GABA blockers.

Quantification of the levels of agonists or antagonists represents another use of the labeled compounds of the present invention. The agonists or antagonists are assayed quantitatively by competition as described above, and the concentrations giving competition are compared and evaluated from standard competition curves with known amounts of known compounds.

Binding data from saturation experiments using increasing concentrations of hot ligand are analyzed using the collection of computer programs described by McPherson (McPherson, G. A., *J. Pharmacol. Methods* 14:213–228 (1985)).

Thus, the tritiated compounds of the invention can be employed as radioactive markers in the titration of pest GABA receptors, in the measurement of the affinity of test compounds for pest GABA receptors, in the titration of known pesticides, and in the study of the distribution and metabolism of said pesticides.

Several experimental methods enable the determination of the affinity of a ligand for its receptors or binding proteins. In particular, a direct method can be used if the ligand under consideration is radioactively marked, or even by competition with a radioactive ligand if the ligand under consideration is not radioactively marked.

A good radioactive ligand must, on the one hand, have a high affinity for its receptors and binding proteins and, on the other hand, have low fixing on any other molecule. In addition, it must be sufficiently stable to be useful in practice.

In particular, the present invention relates to a new radioactive ligand, as defined above, preferably having a specific activity of greater than 30 Ci/mmole and preferably at least equal to 50 Ci/mmole, or approximately 1875 GBq/mmole.

For example, the radioactive marker of the invention can be used during the purification of pest GABA receptors using conventional methods; it is sufficient to add to the cells or to the tissue extract, used as starting products, a determined quantity of the radioactive ligand. The pest GABA receptors are thus marked and their presence or their absence in a given fraction can easily be marked.

The present invention also relates to the use of radiolabeled compound of Formula I as (1) a radioactive marker to locate, titrate or mark pest GABA receptors; or (2) as a radioactive marker to measure the affinity of agonists or antagonists of pest GABA (competition experiments) and thus provide an estimation of their biological activity.

The radioactive marker of the present invention can also be used in the study of the mechanism for intracellular action and of the general mechanism of compound of Formula I in vivo and in the cells and cellular extracts, and also for studying the in vivo as well as cellular and subcellular distribution of said compounds and of pest GABA inhibitors in general.

Compounds are screened for GABA inhibiting activity using in vitro assays that measure the ability of a test compound to bind to pest and/or mammalian GABA receptors. These assays, exemplified hereinbelow, employ membranes possessing active GABA receptors. Immediately following is a description of methods for forming such membranes.

Preparation of Housefly Membranes Possessing Active GABA Receptors

Newly emerged houseflies (Musca domestica, available from Rincon-Vitova Insectaries, Inc., Ventura, Calif.) were sedated with carbon dioxide gas, collected in 50 mL polypropylene conical tubes, and immediately frozen by submersion in liquid nitrogen. Unless specified, all of the following work was performed at 0–4° C. After removal from liquid nitrogen, the tubes of frozen houseflies were shaken vigorously by hand to decapitate the houseflies. The decapitated houseflies were then passed through a #10 mesh tissue sieve to separate the heads, which went through the sieve, from the larger abdomen, thoraxes, and residual intact houseflies that did not pass through the sieve. Contaminating wings were removed by holding a vacuum nozzle approximately 4 cm above the heads, and contaminating legs were separated from the heads by passage through a #15 mesh screen. All remaining debris were removed from the pool of heads using forceps. The purified heads were collected in 50 mL polypropylene conical tubes and stored in liquid nitrogen until processed further.

About 13 g of purified housefly heads were suspended in about 65 mL of 10% sucrose buffer (10% sucrose (w/w) in 10 mM Tris, pH 7.5). The heads were homogenized for about 1 minute, using a Tissumizer™ homogenizer equipped with a SDT-100EN probe (available from Tekmar-Dohrmann, Cincinnati, Ohio) running at 70% of its maximum speed. The extract was further homogenized by about 5 passes through a 40 mL Dounce tissue grinder. The extract was then centrifuged at about 500×g for about 5 minutes to pellet large debris. The supernatant was collected; the pellet was washed with an additional 65 mL of 10% sucrose buffer and centrifuged at 500×g for about 5 minutes. The second supernatant was collected and combined with the first supernatant, and the pool was filtered through a 100µCell-MicroSieve™ mesh to remove residual debris (available from BioDesign of New York, Carmel, N.Y.).

Neuronal membranes containing active GABA receptors were collected via sucrose density centrifugation by the following method. About 8 mL of 35% sucrose buffer (35% sucrose (w/w) in 10 mM Tris, pH 7.5), were dispensed into each of six 38 mL ultracentrifuge tubes. These layers were overlaid with about 8 mL of 20% sucrose buffer (20% sucrose (w/w) in 10 mM Tris, pH 7.5), and finally overlaid with about 20 mL of filtered extract supernatant. The tubes were centrifuged at about 120,000×g for about 100 min at 4° C. After centrifugation, the 10% sucrose layer and most of the 20% sucrose layer were removed by aspiration. The membranes at the interface of the 20% sucrose and 35% sucrose layers were collected, pooled, diluted with 10% sucrose buffer, and centrifuged at about 120,000×g for about 40 min at 4° C. After centrifugation, the supernatant was discarded, and the pellets resuspended in about 6.5 mL of assay buffer (10 mM phosphate, 300 mM NaCl, pH 7.5) using a 10 mL Potter-Elvehjem tissue grinder with a Teflon® pestle. Protein concentration was determined by the Bio-Rad Protein Assay (available from Bio-Rad Laboratories, Hercules, Calif.) using bovine serum albumin as a standard. The membranes were aliquoted and stored in liquid nitrogen for up to 2 months before use.

Preparation of Mouse Brain Membranes Possessing Active GABA Receptors

Mouse brains were obtained from carbon dioxide-asphyxiated Swiss-Webster mice, washed with phosphate-buffered saline, and used either fresh or after storage at −80° C. for up to 10 months. Unless specified, all preparation steps were performed at 0–4° C. For each preparation, 20 brains were suspended in about 40 mL of 0.32 M sucrose and homogenized for about 2 minutes, using a Tissumizer™ homogenizer equipped with a SDT-100EN probe (available from Tekmar-Dohrmann, Cincinnati, Ohio) running at 50% of its maximum speed. The extract was centrifuged for about 5 min at about 1000×g to pellet intact brain tissue. The supernatant was retained and the pellet washed with an additional 40 mL of 0.32 M sucrose and centrifuged at 1000×g for about 5 minutes. The 1000×g supernatants were combined and centrifuged at about 10,000×g for about 20 min to pellet membranes. The 10,000×g supernatant was discarded and the pellet was resuspended in about 20 mL of water containing 1 mM EDTA. The sample was dialyzed two times for about 3 hours each against about 3 L of water. The sample was then centrifuged at about 25,000× for about 30 min to pellet the membranes. After centrifugation, the supernatant was discarded and the pellet recovered. The protein concentration of the pellet was determined by the Bio-Rad Protein Assay (available from Bio-Rad Laboratories, Hercules, Calif.) using bovine serum albumin as a standard. The membranes were aliquoted and stored at −80° C. for up to 6 months before use.

In vitro Assay to Screen Compounds for Ability to Bind Housefly GABA Receptors

Housefly neuronal membranes are prepared as described above from housefly heads. Test compounds are dissolved in dimethylsulfoxide (DMSO) at concentrations ranging from about 2 nM to about 100 mM. About 1 µL of a dissolved test compound is dispensed into a well of a 96-well polystyrene plate. About 100 µL of ice cold assay buffer (10 mM phosphate, 300 mM NaCl, pH 7.5) containing 10.4 nM 5-amino-4-cyano-3-[$^3$H$_3$]methylthio-1-(2,6-dichloro-4-trifluoromethyl)pyrazole (Compound 1, 82.5 Ci/mmol) is added to the well, followed by about 100 µL of ice cold assay buffer containing about 0.5–1.0 mg/mL housefly neuronal membranes. Control wells are prepared the same way except that the housefly neuronal membranes were omitted from the "negative" wells, and the test compounds are omitted from the "positive" wells. The samples are incubated for about 45 min at about 24° C. and then filtered on a 0.1% (w/v) polyethylenimine-soaked glass fiber Filtermat A (available from EG&G Wallac Inc., Gaithersburg, Md.) followed by four 100 mL rinses of cold assay buffer using a Harvester 96® cell harvester (available from Tomtec, Orange, Conn.). The filtermat is air dried and radioactivity bound to the filtermat was detected with either a 1450 MicroBeta® Trilux scintillation counter (available from EG&G Wallac Inc.) or a Topcount NXT™ scintillation counter (available from Packard Instrument Co., Meriden, Conn.) using standard methods.

Specific binding is considered to be the difference between total $^3$H bound to the neuronal membranes in the absence of any inhibitors and nonspecific $^3$H bound to the neuronal membranes upon the addition of 10 μM unlabeled compound 1. The average radioactivity contained in the "negative" wells is subtracted from each of the assay wells. Compounds that displace $^3$H-compound 1 specifically bound to the housefly neuronal membranes are tested at 24–48 different final concentrations, varying from about 0.1 nM to about 125 μM, in order to determine the concentration at which 50% of the maximum inhibition due to the addition of that compound is observed (IC$_{50}$). This value is calculated by plotting the data on a log-linear plot and either dropping a line to the x-axis perpendicular to a line drawn to the y-axis at approximately 50% inhibition of $^3$H-compound 1 binding, or by fitting the data to the formula I=XY/(X+Z), in which I is the percent inhibition of $^3$H-compound 1 binding, X is the inhibitor concentration, Y is the maximum percent inhibition of $^3$H-compound 1 binding observed, and Z is the calculated IC$_{50}$.

In vitro Assay to Screen Compounds for Their Ability to Bind Mouse Brain GABA Receptors Mouse brain membranes are prepared as described above from dissected mouse brains. Test compounds are dissolved in dimethylsulfoxide (DMSO) at concentrations ranging from about 2 nM to about 100 mM. About 1 μL of a dissolved test compound is dispensed into a well of a 96-well polystyrene plate. About 100 μL of ice cold assay buffer (10 mM phosphate, 300 mM NaCl, pH 7.5) containing 10.4 nM compound 1 (82.5 Ci/mmol) is added to the well, followed by about 100 μL of ice cold assay buffer containing about 0.25–0.5 mg/mL mouse brain membranes. Control wells are prepared the same way except that the mouse brain membranes are omitted from the "negative" wells, and the test compounds are omitted from the "positive" wells. The samples are incubated for about 45 min at about 24° C. and then filtered on a 0.1% (w/v) polyethylenimine-soaked glass fiber Filtermat A (available from EG&G Wallac Inc., Gaithersburg, Md.) followed by four 100 mL rinses of cold assay buffer using a Harvester 96® cell harvester (available from Tomtec, Orange, Conn.). The filtermat is air dried and radioactivity bound to the filtermat is detected with either a 1450 MicroBeta® Trilux scintillation counter (available from EG&G Wallac Inc.) or a Topcount NXT™ scintillation counter (available from Packard Instrument Co., Meriden, Conn.) using standard methods.

Specific binding is considered to be the difference between total $^3$H bound to the mouse brain membranes in the absence of any inhibitors and nonspecific $^3$H bound to the mouse brain membranes upon the addition of 10 μM unlabeled compound 1. The average radioactivity contained in the "negative" wells is subtracted from each of the assay wells. Compounds that displace $^3$H-compound 1 specifically bound to the mouse brain membranes are tested at 24–48 different final concentrations, varying from about 1 nM to about 125 μM, in order to determine the concentration at which 50% of the maximum inhibition due to the addition of that compound is observed (IC$_{50}$). This value is calculated by plotting the data on a log-linear plot and either dropping a line to the x-axis perpendicular to a line drawn to the y-axis at approximately 50% inhibition of $^3$H-compound 1 binding, or by fitting the data to the formula I=XY/(X+Z), in which I is the percent inhibition of $^3$H-compound 1 binding, X is the inhibitor concentration, Y is the maximum percent inhibition of $^3$H-compound 1 binding observed, and Z is the calculated IC$_{50}$.

Preparation of Compounds

A fourth aspect of the present invention relates to a method for the preparation of radiolabeled compounds having Formula I.

The synthesis of radioactive material 1 is carried out according to the protocol shown in Scheme 1.

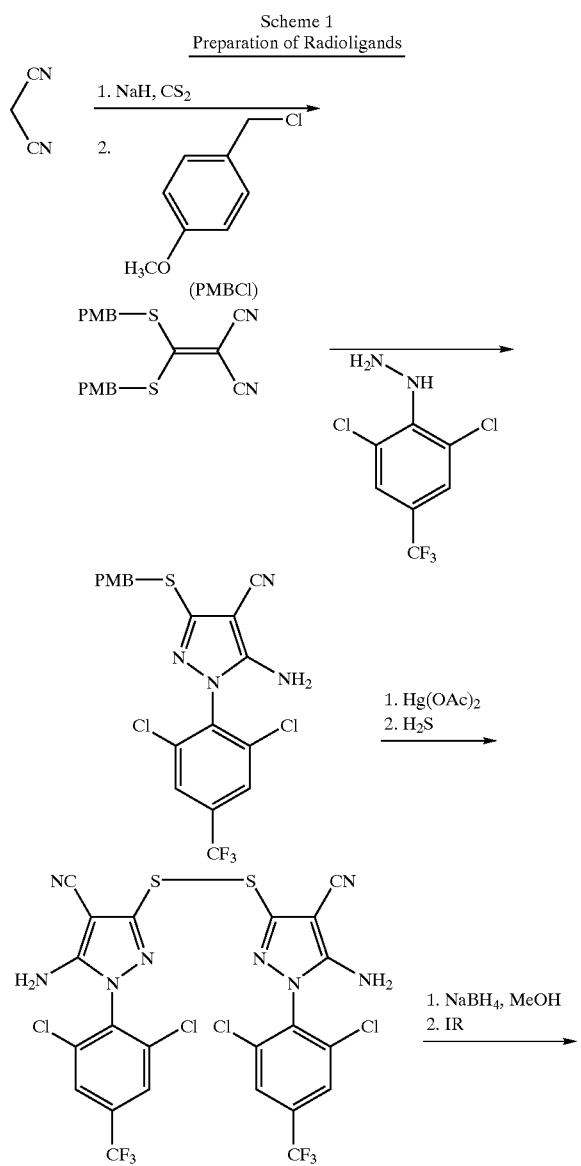

-continued

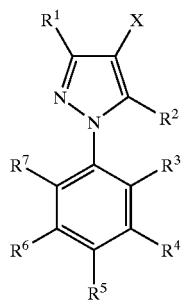

where R is $^3H_3C$, $^2H_3C$, $H_3{}^{14}C$, $H_3{}^{13}C$, $^2H_3{}^{14}C$, $^2H_3{}^{13}C$, $^3H_3{}^{14}C$, or $^3H_3{}^{13}C$.

Additional methods for preparing tritiated compounds, including catalytic dehalogenations with tritium, can be found in Filer, *Isotopes in the Physical and Biomedical Sciences, Vol. 1, Labeled Compounds (Part A)*, Chapter 6, see especially Section 2.

Isotopic hydrogen can be introduced into organic molecules by synthetic techniques and exchange techniques. Synthetic techniques, where tritium or deuterium is directly and specifically inserted, yield high tritium or deuterium abundance, but can be limited by the chemistry required. In addition, the molecule being labeled may be changed, depending upon the severity of the synthetic reaction employed. Exchange techniques yield lower tritium or deuterium incorporation, often with the isotope being distributed over many sites on the molecule, but offer the advantage that they do not require separate synthetic steps and are less likely to disrupt the structure of the molecule being labeled.

Three synthetic methods for incorporating activity levels of tritium into target molecules include: (1) "hydrogenation" of the target molecule using tritium gas ($T_2$), with a catalyst; (2) tritiodehalogenation; and (3) tritiomethylation with $CT_3I$. A fourth way of synthetically incorporating tritium into a target molecule which contains a reducible site is to contact the target molecule with a reducing agent which is capable of inserting one or more tritium atoms into the reducible site. This methodology essentially mimics reduction with hydrogen-inserting reducing agents. A final way of synthetically incorporating tritium into a target molecule which contains a reducible site is to employ in situ synthesis to generate a highly reactive alkali metal deuteride or tritide with a large proportion of its hydrogen present as deuterium or tritium from the respective deuterium or tritium gas. This material is then converted into a desirable highly selective labeling agent. See, for example, Andres et al., U.S. Pat. No. 5,186,868.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:
1. A radiolabeled compound of Formula I:

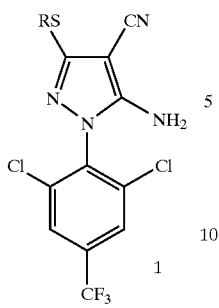

I or a salt thereof, where
$R^1$ represents $R^8$, $R^8O$, $R^8SO_2$, $R^8SO$ or $R^8S$ in which $R^8$ is tritiated methyl, deuterated methyl, [$^{13}C$]methyl or [$^{14}C$]methyl;
X is halo, cyano, $C_{1-6}$ alkoxycarbonyl, $C_{2-6}$ alkynyl, optionally substituted $C_{6-14}$ aryl or an optionally substituted 5- to 7-membered heteroaromatic ring linked to thiazole via a carbon-carbon bond;
$R^2$ is hydrogen or amino; and
$R^3$–$R^7$ each represent hydrogen, halogen, straight- or branched-chain $C_{1-4}$ alkyl or $C_{1-4}$ alkoxy, either of which is unsubstituted or substituted by one or more halogen atoms, straight- or branched-chain $C_{1-4}$ alkylthio or $C_{1-4}$ alkylsulphinyl, either of which is substituted by one or more halogen atoms, nitro, cyano, or straight- or branched-chain $Ci_{1-4}$ alkylsulphonyl group which is unsubstituted or substituted by one or more halogen atoms.

2. The compound of claim 1, wherein $R^1$ is —$SC^3H_3$, —$SOC^3H_3$, —$SO_2C^3H_3$, —$S^{14}CH_3$, —$S^{13}CH_3$, —$S^{13}C^2H_3$, or —$SC^2H_3$.

3. The compound of claim 2, wherein $R^1$ is —$SC^3H_3$.

4. The compound of claim 1, wherein X is cyano, chloro, iodo, $C_{1-4}$ alkoxycarbonyl or $C_{2-4}$ alkynyl.

5. The compound of claim 1, wherein X is cyano.

6. The compound of claim 1, wherein X is $C_{6-14}$ aryl or a 5- to 7-membered heteroaromatic ring linked to thiazole via a carbon-carbon bond, either of which is optionally substituted by one or more of halogen, trifluoromethyl, hydroxy, $C_{1-4}$ alkoxy, $C_{1-4}$ alkylthio, $C_{1-4}$ alkylsulfinyl, amino, nitro, cyano, $C_{2-6}$ carboxyalkyl, amidine, tetrazolyl, mono- or di-($C_{1-6}$)alkylamino, mono- or di-($C_{6-10}$) arylamino, $C_{6-10}$ arylthio, $C_{6-10}$ arylsulfonyl, $C_{6-10}$ arylsulfinyl, oxime, $C_{6-10}$ aryl hydrazone, aminocarbonyl, mono- or di-($C_{1-6}$)alkylaminocarbonyl, carboxyamino, $C_{1-6}$ alkoxycarbonylamino, $C_{6-10}$aryloxycarbonylamino, $C_{7-11}$ aralkoxycarbonylamino, mono- or di-($C_{1-6}$) alkylaminothiocarbonyl, or combinations thereof.

7. The compound of claim 1, wherein X is phenyl, naphthyl, pyridyl, thienyl, furanyl, isoxazolyl, thiazolyl, isothiazolyl, indolizinyl, isoindolyl, indolyl, indazolyl, quinolizinyl, quinolinyl, or isoquinolinyl, any of which is optionally substituted by one or more of halogen, $C_{1-4}$ alkoxy, $C_{1-4}$ haloalkoxy, $C_{1-4}$ alkoxycarbonyl, nitro, amino, cyano, $C_{1-4}$ alkylthio, $C_{1-4}$ alkylsulfinyl or $C_{1-4}$ alkylsulfonyl.

8. The compound of claim 1, wherein X is 3-methyloxadiazin-5-yl, thiophen-2-yl; thiophen-3-yl, 5-methylthiophen-2-yl, 4-methylthiophen-2-yl, 5-chlorothiophen-2-yl, 4-chlorothiophen-2-yl, 5-methylcarbonylthiophen-2-yl, benzothiophen-2-yl, pyrimidin-6-yl, pyrazin-6-yl, phenyl, 2-methylphenyl, 2-fluorophenyl, 2-chlorophenyl, 2-trifluoromethylphenyl, 2-cyanophenyl, 2-methoxyphenyl, 2-methylthiophenyl, 2,4-dimethoxyphenyl, 3-methylphenyl, 3-isopropylphenyl, 3-methoxyphenyl, 2-fluorophenyl, 2-chlorophenyl, 2-trifluoromethylphenyl, 2-cyanophenyl, 2-methoxyphenyl, 2-methylthiophenyl, 3,5-di(trifluoromethyl)phenyl, 3-chloro-4-fluorophenyl, 3,4-dimethoxyphenyl, 3,4,5-trimethoxyphenyl, 1,3-benzodioxazol-5-yl, 4-methylphenyl, 4-fluorophenyl, 4-chlorophenyl, 4-bromophenyl, 4-trifluoromethylphenyl, 4-cyanophenyl, biphenyl, 4-isopropylphenyl, 4-methoxyphenyl, or 4-methylthiophenyl.

9. The compound of claim 1, wherein $R^2$ is hydrogen.

10. The compound of claim 1, wherein $R^2$ is $NH_2$.

11. The compound of claim 1, wherein $R^3$ is halogen;

$R^4$ is hydrogen;

$R^5$ is hydrogen, $C_{1-6}$ alkyl optionally substituted by one or more halogen atoms, $C_{1-6}$ alkoxy, optionally substituted by one or more halogen atoms or $SF_5$;

$R_6$ is hydrogen; and $R^7$ is halogen.

12. The compound of claim 1, wherein $R^3$, $R^5$ and $R^7$ are chloro; and $R^4$ and $R^6$ are hydrogen;

$R^3$ is chloro; $R^5$ is trifluoromethyl; and $R^4$, $R^7$, and $R^6$ are hydrogen;

$R^3$ is bromo; $R^5$ is trifluoromethyl; and $R^4$, $R^7$, and $R^6$ are hydrogen;

$R^3$ is bromo; $R^5$ and $R^7$ are trifluoromethyl; and $R^4$ and $R^6$ are hydrogen;

$R^3$ and $R^7$ are chloro; $R^5$ is trifluoromethyl; and $R^4$ and $R^6$ are hydrogen; or $R^3$ and $R^7$ are bromo; $R^5$ is trifluoromethyl; and $R^4$ and $R^6$ are hydrogen.

13. The compound of claim 1, wherein $R^3$ and $R^7$ are chloro; $R^5$ is trifluoromethyl; and $R^4$ and $R^6$ are hydrogen; or $R^3$ and $R^7$ are bromo; $R^5$ is trifluoromethoxy; and $R^4$ and $R^6$ are hydrogen.

14. A composition comprising an effective amount of the radiolabeled compound of claim 1 for use in receptor binding and a suitable carrier.

15. A composition comprising an effective amount of the radiolabeled compound of claim 5 for use in receptor binding and a suitable carrier.

16. A composition used to evaluate the mechanism of neurotransmitter hypofunction and hyperfunction in a pest comprising an effective amount of the radiolabeled compound of claim 1 as an active ingredient.

* * * * *